United States Patent
Jia

(10) Patent No.: US 8,113,836 B2
(45) Date of Patent: Feb. 14, 2012

(54) DENTAL MATERIAL AND METHODS OF USE

(75) Inventor: Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 0 days.

(21) Appl. No.: 12/966,014

(22) Filed: Dec. 13, 2010

(65) Prior Publication Data

US 2011/0129802 A1  Jun. 2, 2011

Related U.S. Application Data

(62) Division of application No. 11/755,933, filed on May 31, 2007, now abandoned.

(51) Int. Cl.
*A61C 5/02* (2006.01)
*A61K 6/08* (2006.01)

(52) U.S. Cl. ............. 433/204; 433/228.1; 523/116; 523/117

(58) Field of Classification Search ......... 433/204, 433/228, 1; 523/116, 117
See application file for complete search history.

(56) References Cited

U.S. PATENT DOCUMENTS

| | | | |
|---|---|---|---|
| 2,300,064 A | 10/1942 | Rosen et al. | 525/210 |
| 2,718,691 A | 9/1955 | Sussenbach | 277/316 |
| 3,066,112 A | 11/1962 | Bowen | |
| 3,076,777 A | 2/1963 | Zeolla et al. | 524/525 |
| 3,179,623 A | 4/1965 | Bowen | |
| 3,194,784 A | 7/1965 | Bowen | |
| 3,472,770 A | 10/1969 | Preston et al. | 508/122 |
| 3,751,399 A | 8/1973 | Lee et al. | |
| 3,926,906 A | 12/1975 | Lee et al. | |
| 4,558,875 A | 12/1985 | Yamaji et al. | 277/312 |
| 4,717,341 A | 1/1988 | Goldberg et al. | |
| 4,894,012 A | 1/1990 | Goldberg et al. | |
| 5,051,130 A * | 9/1991 | Futami et al. | 106/35 |
| 5,157,079 A | 10/1992 | Duck et al. | 525/113 |
| 5,276,068 A | 1/1994 | Waknine | |
| 5,437,878 A | 8/1995 | Panhorst et al. | 426/4 |
| 5,455,285 A | 10/1995 | Carroll | 523/109 |
| 5,564,929 A | 10/1996 | Alpert | |
| 5,919,044 A | 7/1999 | Sicurelli et al. | |
| 6,030,220 A | 2/2000 | Karmaker et al. | |
| 6,039,569 A | 3/2000 | Prasad et al. | |
| 6,186,791 B1 | 2/2001 | Karmaker et al. | |
| 6,220,863 B1 * | 4/2001 | Kamohara et al. | 433/224 |
| 6,428,319 B1 | 8/2002 | Lopez et al. | |
| 6,447,297 B1 | 9/2002 | Lopez et al. | |
| 6,455,608 B1 | 9/2002 | Jia et al. | |
| 6,537,563 B2 | 3/2003 | Jia et al. | |
| 6,555,130 B2 | 4/2003 | Wustling et al. | 424/448 |
| 7,086,864 B2 | 8/2006 | Lopez et al. | |
| 7,163,401 B2 | 1/2007 | Karmaker et al. | |
| 7,168,952 B2 | 1/2007 | Karmaker et al. | |
| 7,204,874 B2 | 4/2007 | Jia et al. | |
| 7,204,875 B2 | 4/2007 | Jia et al. | |
| 7,211,136 B2 | 5/2007 | Jia et al. | |
| 2001/0039302 A1 | 11/2001 | Wustling et al. | 523/351 |
| 2002/0019456 A1 | 2/2002 | Jia | |
| 2003/0124483 A1 | 7/2003 | Jia et al. | 433/81 |
| 2004/0253433 A1 | 12/2004 | Pearce et al. | 428/304.4 |
| 2005/0066854 A1 | 3/2005 | Jia | |
| 2005/0221039 A1 | 10/2005 | Dunlap et al. | 428/36.9 |
| 2006/0293424 A1 | 12/2006 | Tse et al. | 524/270 |
| 2007/0111878 A1 | 5/2007 | Zuberi et al. | 501/95.1 |
| 2007/0184405 A1 | 8/2007 | Jia et al. | |

FOREIGN PATENT DOCUMENTS

JP   357106615 A   7/1982

* cited by examiner

*Primary Examiner* — Tae H Yoon
(74) *Attorney, Agent, or Firm* — Cantor Colburn LLP

(57) ABSTRACT

A dental filling material comprising a polybutylene polymer having a molecular weight of about 10,000 to about 100,000 and being viscoelastic at about 20° C. The composition may include other polymeric resins, fillers, plasticizers and other additives typically used in dental materials. The filling material is used for the filing of root canals.

19 Claims, 2 Drawing Sheets

DENTAL MATERIAL AND METHODS OF USE

This application is a divisional application of U.S. Ser. No. 11/755,933, filed on May 31, 2007, now abandoned.

FIELD OF THE INVENTION

This invention relates to dental material compositions suitable for dental filling and/or sealing applications, especially for use in root canal treatments.

BACKGROUND OF THE INVENTION

Endodontics or root canal therapy is that branch of dentistry that deals with the diseases of the dental pulp and associated tissues. One aspect of endodontics comprises the treatment of infected root canals, the removal of diseased pulp tissues, followed by the biomechanical modification and the subsequent filling of the pulp cavity (root canal). Root canal therapy is generally indicated for teeth having sound external structures but having diseased, dead or dying pulp tissues. Such teeth may or may not generally possess intact enamel and dentin and are satisfactorily engaged with bony tissue. In such teeth, the pulp tissue and excised portions of the root should be replaced by a biocompatible substitute.

One technique for the preparation of a root canal involves creating a coronal access opening with a conventional dental drill. A tool is used for gross removal of pulp material from the root canal through the coronal access opening. The void formed is enlarged with reamers and/or files to result in a fully excavated cavity. Debris is removed from this cavity by flushing and the cavity is cleansed to remove all diseased tissue. This process, while essential, results in a root canal that is weakened and susceptible to fracture. Following chemical antisepsis, the excavated canal is ready for filling.

A basic method involves inserting a filling cone into a root canal and cementing therein to obturate the canal. The common root canal filling cone material is made from gutta-percha. Lateral condensation is a method in which several filling cones, a primary cone and auxiliary cones, are inserted into a root canal. The primary cone is inserted and cemented to the seat of the root canal. Using a tapered spreader, the primary cone is then squeezed against the side of the root canal and a second cone is inserted and cemented into place. This process is continued until the root canal is completely obturated which can require up to 10 to 15 filling cones. Vertical condensation of warm or hot gutta-percha is yet another method of sealing root canals. After cementing a primary cone short of the apex of the root canal, heat application is alternated with a series of smaller and smaller pluggers until the gutta-percha is moved to the apex. This is often possible when the smallest plugger approaches the apex of the tooth within 3 to 5 millimeters. The space is then backfilled. Lateral canals are packed and sealed as a consequence of lateral expansion of a wave of heated gutta-percha. Alternatively, small segments of gutta-percha can be used in this method that are inserted into the root canal, heated in order that they can adhere to one another and each backfilled one at a time until the root canal is filled. All three of these methods, the single filling cone, lateral condensation and vertical condensation apply root canal cement or sealer around the individual cones or in between segments as a binding agent.

Another method employs an injection gun that injects warm or hot gutta-percha filling material into a root canal. The injector initially places heated gutta-percha at the apical area of the root canal through a needle-like canula tip and fills the gutta-percha into any surrounding voids/spaces under pressure or at the seat of the root canal which is then condensed with a plugger into the root tip. The injector then backfills the root canal by injecting additional gutta-percha into the root canal until it is obturated. A similar method involves heating gutta-percha on a flexible metal or plastic carrier used to insert the gutta-percha into the root canal. The carrier may be a solid rod, or a hollow rod, situated in the center of a master cone. The rod is connected to a handle which may be removed by slipping it out of the hollow rod, or cutting it off if it is a solid rod.

Most of the current methods employed in obturating a canal use a gutta-percha material or Resilon® material, a new type of synthetic thermoplastic material based on a polyester resin, available from Pentron Clinical Technologies, LLC. It has been a challenge for dentists to control the exact amount of the material within the border of the root canal to avoid overfilling. When cold (at ambient temperature or at the temperature of the oral cavity), the gutta-percha is not malleable so it cannot be molded to the canal walls, resulting in poor adaptation.

On the other hand, when heated beyond the melting temperature of the filling materials, the molten gutta-percha cools down to body temperature in the root and a uniform contraction takes place, which is typical behavior of a thermoplastic material behaves. This can reduce adherence to the walls of the canal and it often results in a less than ideal seal. A publication entitled "Analysis Of Shrinkage Of Different Gutta-Percha Types Using Optical Measurement Methods" in Schweiz Monatsschr Zahnmed, 2006; 116(4):356-61, has shown that commercial dental gutta percha materials have the volume shrinkage of about 6.5-7.3% when heated to about 90° C. and cooled down to about 35° C. Due to poor adaptation to the canal wall or dimensional change caused by volume shrinkage, leakage may result, which facilitates the bacteria to enter the canal from the mouth, which can lead to the persistence of an infection or other complications.

It is preferable that the root canal filling material have proper flexibility, malleability and ease of use. It would be advantageous to provide a root canal filling material having good retrievability and/or dissolvability. It would be highly advantageous to provide a root canal filling material that could be inserted without the need for heating to soften it, thereby eliminating volume shrinkage due to melting and cooling. It would be beneficial if a cavity filling material and root canal filling material could easily flow into the crevices and accessory canals in the root canal and form intimate contact with the surface adjacent to it. It would be further advantageous if the root filling material strengthened the root.

SUMMARY OF THE INVENTION

These and other objects and advantages are accomplished by the filling material of the present invention comprising a polybutylene polymer. Additional materials may be included therewith such as other polymeric resins, fillers, plasticizers, adhesives and other additives typically used in dental filler materials.

In one embodiment herein, the filling material is used for the filling of root canals. The material may be placed in a root canal that has been opened to a predetermined dimension by use of endodontic files, to seal the apical end. If necessary, the filling material can be compacted toward the apex to ensure the apex is adequately sealed, since the filling material exhibits a "cold flow" or self-leveling property at about 20° C. and above.

In yet another embodiment herein, the filling material is fabricated in the form of dental appliances including dental obturators and endodontic posts. The outer layer is fabricated of the material described herein and the core section is made of a different material to give support to the outer layer and provide integrity to the device. In an obturator, the core section forms the shaft of the obturator and the outer layer section forms the filling material on the obturator. In an endodontic post, the core section forms the post section of the post and the outer layer section forms the filling tip section of the post.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Figures 1, 2:
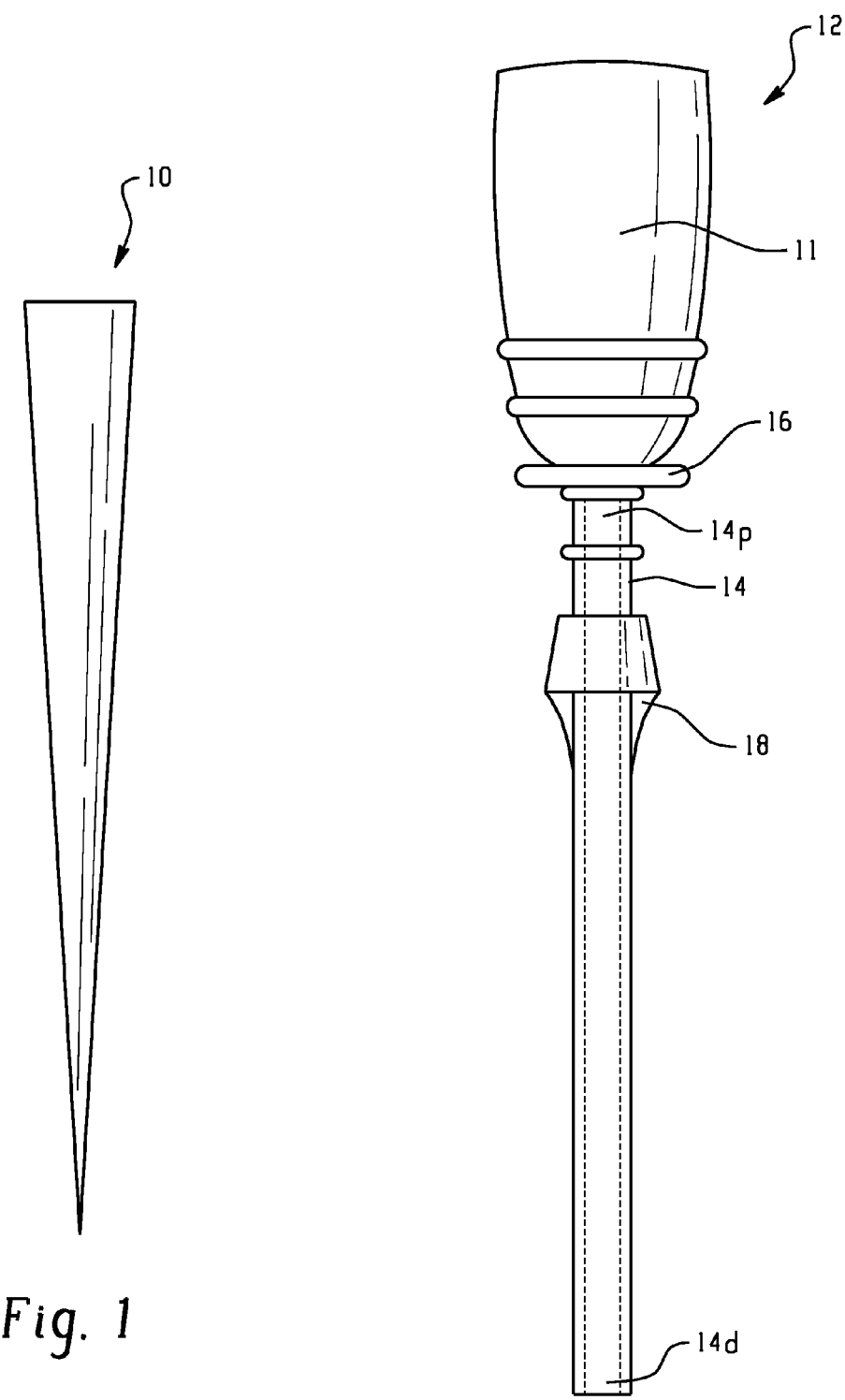
FIG. 1 is an elevational view of a filler cone in accordance with the invention.
FIG. 2 is an elevational view of an appliance having a filling material thereon.

As will be appreciated, the present invention provides a filling material for root canals and cavities comprising a polybutylene polymer with a medium molecular weight (molar mass) of about 10,000 to about 100,000 g/mol. Additional materials may be included therewith such as other polymeric resins, fillers, plasticizers, adhesives and other additives typically used in dental filler materials including, but not limited to, antibiotic, cariostatic, antibacterial, or other anti-inflammatory, biologically active, therapeutic materials, pigments and dyes.

Examples of polybutylene include α-butylene, cis-β-butylene, trans-β-butylene, isobutylene, or their combinations. It is preferable that the medium molecular weight of the polybutylene is in the range of about 10,000 to about 100,000 g/mol. The polybutylenes used herein exhibit very good self-leveling or "cold-flow" properties at ambient temperature (about 20° C.) or above. They are visco-elastic materials and are able to flow into crevices, voids, irregularities using little or no pressure. This visco-elastic property allows them to behave like a molten polymer even when not heated to its melting temperature. This property is also described as "cold flow" since it allows the polymer to flow at ambient or cold temperature without having to heat it. The polybutylenes used herein are very adhesive. In addition thereto, they are insoluble in water and can serve as a gas and moisture barrier. These materials can be easily dissolved in non-polar solvents, such as toluene, hexane as well as polar solvents such as methylene chloride, acetone or the like, for easy cleaning or removal. In addition to root canal filling materials, the materials herein may be used for sealing, temporary cavity fillings, luting and cementing of dental materials.

Examples of commercially available polybutylenes include OPPANOL B 10, OPPANOL B 12 and OPPANOL B 15 series materials from BASF Chemical Company. The average molecular weight of the polyisobutylene products under the product code of OPPANOL B 10, 12 and 15 are about 40,000, 55,000 and 85,000, respectively. Molecular weight with regard to such polybutylene polymers, in particular, refers to the viscosity average molar mass or M. Additional materials may be included therewith such as other polymeric resins, fillers, plasticizers, adhesives and other additives typically used in dental filler materials including, but not limited to, antibiotic, cariostatic, antibacterial, or other anti-inflammatory, biologically active, therapeutic materials, pigments and dyes.

Fillers may be included in the polybutylene composition in an amount up to about 90 percent by weight. Examples include bioglass, calcium phosphate, Portland cement, hydroxyapatite, tricalcium phosphate, a di- or polyphosphonic acid, an anti-estrogen, a sodium fluoride preparation, a substance having a phosphate to calcium ratio similar to natural bone, bone chips, bone crystals, mineral fractions of bone or teeth, calcium hydroxide, other suitable calcium-containing compounds, and the like, silica, silicate glass, quartz, zinc oxide, barium sulfate, barium silicate, strontium silicate, barium borosilicate, strontium borosilicate, borosilicate, lithium silicate, amorphous silica, bismuth compounds such as BiOCl, $Bl_2O_3$, ammoniated or deammoniated calcium phosphate and alumina, zirconia, tin oxide, and titania, and other known dental/medical fillers. Some of the fillers also act as radiopaque/high refractive index materials, such as apatites, silica glass fillers, calcium silicate based fillers, hydroxyapatites, barium sulfate, bismuth subcarbonate, ytterbium oxide, ytterbium fluoride, ytterbium iodine, bismuth oxide, bismuth fluoride, barium oxide, tantalum oxide, zinc oxide and zirconium oxide. The compositions of the inventive materials have a radiopacity similar to or better than conventional dental gutta-percha materials.

The filler may be in the form of a particulate or fiber and may be in nano, micro or macro form, or mixtures thereof. Fibrous fillers also include, but are not limited to, glass, ceramic, metal, carbon, graphite, and polymeric such as cellulose, polyamide, aramid, polyester, polyaramid, acrylic, vinyl and modacrylic, polyolefin, polytetrafluorethylene, mixtures thereof, as well as other fibers known in the art. The fibers may be of uniform or random length, unidirectional or multidirectional, or randomly dispersed, and may be as short as about 3 to about 4 millimeters (mm) or shorter. The fibers may also be in the form of fabric as set forth in U.S. Pat. No. 6,186,791, or as possible reinforcing fibers, as used in U.S. Pat. Nos. 4,717,341 and 4,894,012 to Goldberg et al., all of which are hereby incorporated by reference.

Examples of additional polymeric resins useful in the filling composition or useful in the inner core material, carrier or post section include, but are not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylenes, polyphenylene sulfides, polyarylsulfides, acrylonitrile-butadiene-styrene copolymers, polyurethane dimethacrylates (hereinafter abbreviated to "UDMA", triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1.6 HDDMA") and polycarbonate dimethacrylate (hereinafter abbreviated "PCDMA") and the like. Among the examples given, the resins containing surface functional groups such as acrylate/methacrylate, epoxy, hydroxyl and others are preferred since they not only serve as plasticizers for the compositions but as adhesive components as well for promoting the bonding between the compound and a sealant. Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al., and commonly assigned U.S. Pat. No. 5,276,068 to Waknine (which are hereby incorporated by reference). An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA").

Examples of plasticizers useful in the filling composition include, but are not limited to, polyol, polyolfin or a mixture thereof. The plasticizer can be incorporated into the composition in the range of up to about 40 percent by weight, preferably up to about 30 percent by weight, and most preferably up to about 20 percent by weight.

In a method for restoring a root canal in accordance herein, the root canal is prepared by the dentist. This can involve inserting endodontic files or reamers into the canal to remove pulp, necrotic tissue, organic debris, and other potential irritants. Thereafter, an etchant is applied to the root canal wall. Examples of etchants include, but are not limited to, organic acids or their derivatives such as an ethylene diamine tetra acetic acid (EDTA) solution, amino acid, acrylic acid, maleic acid, citric acid, tartaric acid, itaconic acid, 5-sulfosalicylic acid, propionic acid, lactic acid and the like; inorganic acids such as phosphoric acid, hydrochloric acid, sulfuric acid, nitric acid, and the like. Useful etchants for the process herein disclosed are described in commonly assigned U.S. Pat. No. 6,537,563, which is hereby incorporated by reference.

In general, the commercial dental etchants used for dentin surface conditioning/etching are all suitable for root canal etching purposes. Commercially available etching gels suitable for this purpose are available from Pentron Clinical Technologies, LLC as 10% phosphoric acid etching gel and 37% phosphoric acid etching gel. Preferably, the etchant is a self-etch bonding agent such as described in commonly owned, copending U.S. Application No. 20020019456, which is hereby incorporated by reference. A commercially available self-etch primer useful herein is NanoBond™ self-etch primer from Pentron Clinical Technologies, LLC. Other examples of commercially available self-etch primer/adhesives are SE Bond™ available from Kuraray, Prompt L-Pop™ available from 3M/ESPE company, and iBond™ available from Kulzer. The resin modified glass ionomer based sealants can also be used in conjunction with the root canal filling material.

Alternatively, if the etchant does not include an adhesive, a bonding agent may further be applied to the walls of the root canal. Examples of bonding materials include, but are not limited to, dental acrylate/methacrylate based resin adhesives. Commercially available bonding agents include, but are not limited to, Bond-It® and Bond-1® bonding agents available from Pentron Clinical Technologies, LLC, All Bond 2™ and One Step™ available from Bisco, Prime & Bond™ available from Dentsply, ScotchBond™ available from 3M, and PermaQuik® available from Ultradent. Thereafter, a sealant is applied into the root canal. Examples of sealants include, but are not limited to, acrylate/methacrylate resin based root canal sealants, epoxy resin based sealants, and the like and the sealants disclosed in commonly assigned U.S. Pat. No. 6,455,608, which is hereby incorporated by reference. Commercially available sealants include Fiberfill™ root canal sealant available from Pentron, AH-26™ available from LD Caulk/Dentsply and EndoRez™ available from Ultradent.

Alternately, one-step adhesives or sealants may be used such as EndoRez™ available from Ultradent or Epiphany™ SE sealant available from Pentron Clinical Technologies, LLC in place of the previous-discussed methods as a single step to replace etching, priming and/or bonding.

After the sealant is applied, the filling material is inserted into the canal. It may applied in a variety of ways including, but not limited to, lateral condensation, vertical condensation of soft material, and single points of material either inserted individually or applied to a carrier and inserted into the canal via the carrier. The filling material may be in the form of a cone to be inserted into a canal. The cone may be inserted into the canal using a file or similar instrument, or it may be attached to a file, shaft or similar carrier which instrument is then inserted into the canal with the cone thereon. Due to the "cold flow" property of the material, it is not necessary to heat it prior to insertion into the canal. If for some reason a practitioner requires additional softening, the material may be further softened by placing in an oven or heater to heat and soften the filling material or chemically treating to soften the material. After insertion, the carrier is removed or the excess of the cone is cut off as in a conventional gutta-percha cone application from the root canal.

The material may be compacted toward the apex without prior softening or heating, to ensure the apex is adequately sealed. This may be done by a backfilling technique whereby, for example, the material is injected into the canal using a device having a needle, such as the Obtura II device available from Obtura/Spartan, Fenton, Mo.

If a post is necessary, it is inserted into the canal to provide added support for the remaining tooth structure. An artificial crown, direct or indirect restoration, fixed-partial denture abutment, etc. can then be placed over the tooth to complete the tooth restoration.

The materials and process described herein provide superior sealing and filling of the root canal. The materials used to seal and fill the root canal fill easily into the root along with crevices and gaps therein to reduce or eliminate leakage of bacteria into the canal. This significantly reduces any avenues for bacteria to travel from the coronal end to the apex, reducing the chance for infection. Moreover, the filling materials described herein are easily removable from the root canal. One example of removing the filling material from the root is by dissolving the material in a solvent such as acetone, chloroform or other chlorinated hydrocarbons, aromatic hydrocarbons, tetrahydrofuran, limonene, eucalyptus oil, xylene, benzene, toluene or a mixture thereof.

Commonly assigned U.S. Pat. Nos. 7,204,874, 7,204,875 and 7,211,136, U.S. Patent Publication No. 20050066854 and U.S. patent application Ser. No. 11/614,233 are directed to root canal filling materials and are hereby incorporated by reference.

If the filling material is integrally formed on a post, as mentioned above, a single post unit will preferably comprise a combined endodontic post and tip of filling material. To use the post unit, the tip of the device need not be softened since the material exhibits "cold flow" properties that allow it to flow into the canal with little or no pressure. If necessary, the material may be further softened by placing in an oven or heater to heat and melt the filling material or chemically treating to soften the material. The device will then be placed in a root canal that has been opened to a predetermined dimension by use of endodontic files, to seal the apical end. If necessary, the filling material can be compacted toward the apex, while it is still in the softened state, to ensure the apex is adequately sealed. The post may then be cemented into place by lining the canal walls with a bonding agent and filling the interface between the post and the walls of the canal with a resin cement such as a dual cure cement, a light cure cement or a self cure cement such as FiberFill™ RCS root canal sealant or Cement-It® Universal cement, both available from Penton Clinical Technologies, LLC in Wallingford, Conn. This will result in a coronal seal of the canal via a resin restorative material and an apical seal of the canal by means of a filling material and sealant. The remaining portion of the post, extending supra-gingivally, will be used to build a core around it. Any excess will be cut off. One length of the device will be longer to accommodate the longer roots in anterior teeth. Another length will be shorter to accommodate smaller roots in the molar region. Various diameters may also be provided to accommodate the different sizes of root canals. The bonded flexible post may strengthen the tooth to prevent subsequent root fractures.

Figure 3:
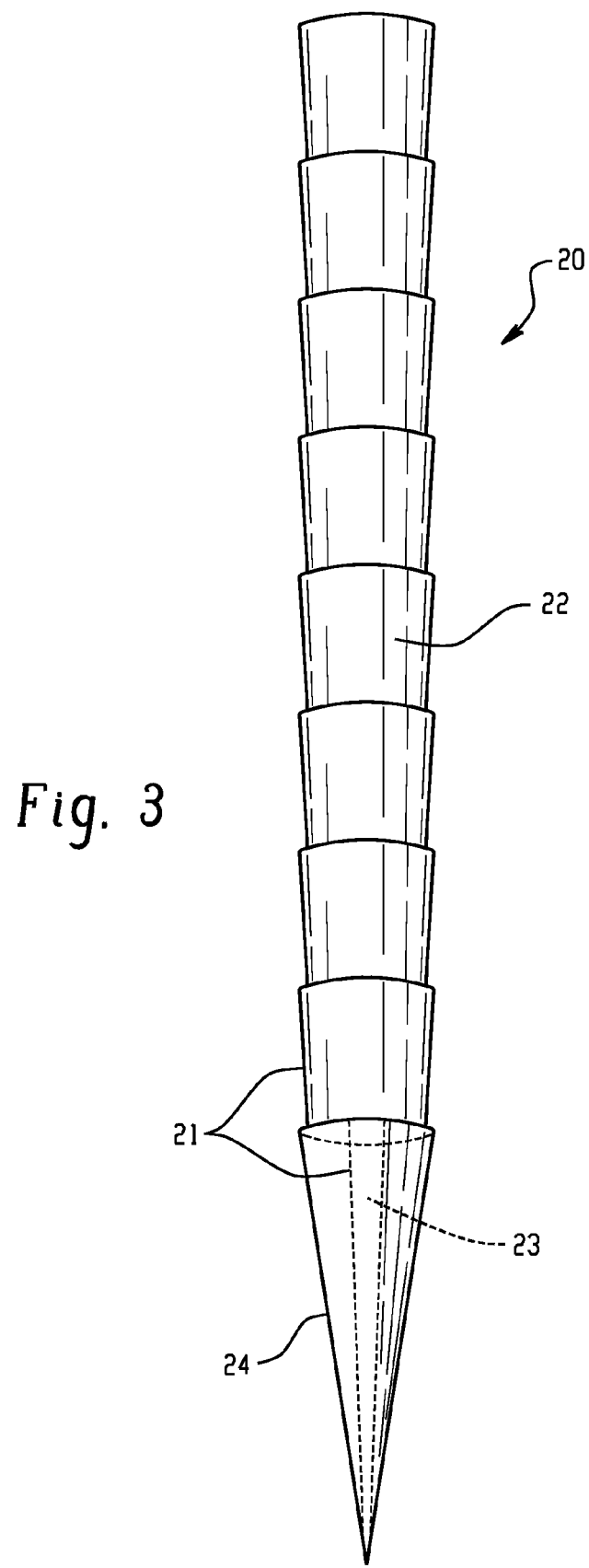
FIG. 3 is an elevational view of a post as an alternate carrier in accordance with the invention.

Reference is made to FIGS. 1 through 3 which filling materials in accordance with the invention. FIG. 1 shows a point 10 fabricated of polybutylene applied to the tip of the carrier. FIG. 2 shows an appliance 12 having a handle 11 and an elongated shaft 14. Shaft 14 has a proximal end 14p and a distal end 14d that fits in a root canal. A sliding support 16 is positioned between shaft 14 and handle 12 to serve as an indicator of the depth of the canal and to help maintain the carrier in place. After the appliance is inserted in the canal, sliding support 16 is moved to the point at the top of the canal. Filling material 18, containing a polybutylene, is positioned on the shaft, starting at the proximal end and continuing down, over the distal end. Reference is hereby made to commonly assigned U.S. Pat. Nos. 6,447,297, 6,428,319, 7,086,864, 7,168,952, and 7,163,401, each directed to posts or obturators having filling materials integrally formed thereon, and all of which are hereby incorporated by reference.

Turning to FIG. 3, a post unit 20 is shown comprising a post section 21 and a cone or tip section 24. Tip section 24 comprises a flexible rod or cone comprising a polybutylene polymer composition for filling the apex of the canal. The filling material may include additives typical in the dental field such as plasticizing, antibiotic, cariostatic, antibacterial, or other anti-inflammatory, biologically active or therapeutic materials.

Post section 21 comprises a main body or endodontic portion 22 and a carrier or apical portion 23, which is located at the apical end of post unit 20. Main body 22 may be a solid rod of circular or other suitable cross-section comprising a substantially smooth surface or may comprise a plurality of frustoconical sections arranged coaxially along the longitudinal axis of main body 22. Preferably, main body 22 has consistent width along the longitudinal axis thereof whereas frustoconical sections each have the same tapered width and same length. It is possible to vary the width and/or length of main body 22 and/or vary the tapered width and/or length of frustoconical sections along the longitudinal axis of main body 22.

Carrier 23 is preferably an extension of main body 22 of post section 21 and is of very fine diameter to accommodate tip section 24 of thermoplastic material of post unit 20. In one method of manufacture which will be discussed hereinafter, post section 21 is manufactured from a rod of material that is cut or machined at the apical end to result in carrier 23 having a very small width or diameter in comparison to main body 22. Carrier 23 is of small diameter to allow enough area to form tip section 24 thereon, and also of enough strength and integrity to accommodate the filling material as discussed above. As stated above, carrier 23 is preferably an extension of main body 22 and is shown having constant diameter along the length thereof, but may be of any shape or size sufficient to hold tip section 24 thereon.

Post section 21 may be fabricated of any material to provide a flexible apical portion and a more rigid endodontic and/or coronal or supracoronal portion, such as metal, plastic, ceramic, polymeric, composite, or other material suitable for placement in the mouth. Composite materials include but are not limited to filler reinforced composite materials and fiber reinforced composite materials comprising the reinforcing component in a polymeric matrix material such as those composite materials listed in U.S. Pat. Nos. 4,717,341 and 4,894,012 to Goldberg et al., U.S. Pat. No. 6,039,569 to Prasad et al., U.S. Pat. No. 6,030,220 to Karmaker et al, U.S. Pat. No. 5,564,929 to Alpert, U.S. Pat. No. 5,919,044 to Sicurelli, Jr. et al., U.S. Pat. No. 7,204,874 to Jia et al, all of which are hereby incorporated by reference.

Examples of metals useful as post section 21 include but are not limited to metals or alloys of Pd, Pt, Rh, Ir, Au, Ag, Ti, Co, Mo and mixtures thereof such as AgPd, AuPtPd, TiAlFe, TiAlV, CoCrMo, stainless steel and brass. Ceramic materials useful in the fabrication of post section 21 include but are not limited to alumina, zirconia, mullite, spinel, porcelain, titania, lithium disilicate, leucite, amorphous glass, lithium phosphate, and combinations thereof, or any high strength ceramic material which can withstand the stresses created in the mouth.

Carrier 23 preferably comprises a smooth surface, although it is in no way limited to such and may be of any surface suitable for application of filling material thereon. The post may be provided in an opaque tooth color or it may be colored similar to a tooth's pulp for enhanced esthetics. The post may include an appropriate amount of radiopaque material such as titanium oxide, barium sulfate, and similar materials known in the dental industry to insure x-ray documentation which may be added to the post material during manufacture thereof. After post section 21 has been manufactured, carrier 23 of post section 21 is then coated with a filling material such as set forth above to obtain cone section 24 thereon. The filling material may be applied by any known means such as dipping, injection molding, hand rolling, and the like.

To use the post unit, the device may be used as is, or may be heated by placing in or near an oven or heater to heat and soften the filling material or dipped in a chemical solution such as chloroform to soften the filling material. The device will then be placed in a root canal that has been opened to a predetermined dimension by use of endodontic files, to seal the apical end. If necessary, the filling material can be compacted toward the apex, while it is still in the softened state, to ensure the apex is adequately sealed. The post is then cemented into place by lining the canal walls with a bonding agent and filling the interface between the post and the walls of the canal with a resin cement, such as a dual cure cement. This will result in a coronal seal of the canal via resin restorative material and an apical seal of the canal by means of filling material and sealant. The remaining portion of the post, extending supra-gingivally, will be used to build a core around it, and if necessary, for placement of a crown thereon. Any excess of the post will be cut off. One length of the device will be longer to accommodate the longer roots in anterior teeth. Another length will be shorter to accommodate smaller roots in the molar region.

It is preferable that the outer layer of material on all the devices and posts herein be symmetrically disposed on the inner core material or section or shaft. The outer layer of material may be overmolded by known techniques including dipping or injection molding. The obturator device may include a washer, such as an elastomeric washer that can slide along the obturator and can be used to measure the depth of the canal into which it is to be inserted. This will aid the practitioner in providing an obturator with the correct length for the patient's root canal.

The method of using the device may include inserting a sealant into the root canal, inserting the obturator into the root canal so that the distal end at least substantially reaches the root canal apical end; and severing the part of the obturator that extends above the coronal end of the root canal. Moreover, the method may further include inserting a size verifier into the root canal to measure the length of the root canal from the root canal apical end, noting the depth of the size verifier in the root using depth indicators, withdrawing the size verifier from the root canal, and moving a depth indicator located on the obturator to correspond to the location of the depth indicator on the size verifier. The obturator may be heated to further soften it prior to insertion into the patient's canal.

The following non-limiting examples illustrate the invention.

Example 1

Commercial polyisobutylene with an average molar mass of about 40,000 g/mol. and 85,000 g/mol. (Oppanol B 10 and Oppanol B 12 respectively, from BASF Chemical Company, Germany) were utilized. Table 1 below illustrates inventive dental filling material compositions.

TABLE 1

| Components | Composition 1 (% by weight) | Composition 2 (% by weight) |
|---|---|---|
| Oppanol B 10 SFN | 40 | |
| Oppanol B 12 SFN | | 40 |
| Bismuthoxy Chloride | 60 | 60 |

To blend the filler into the polybutylene polymer, the polymer was heated at the temperature of about 80° C. to melt it, then the filler was added and mixed until a homogenous putty compound was obtained. The compound was then cooled down to ambient temperature to form the inventive filling material. Alternatively, the polymer can be dissolved by a solvent and filler can be blended thereafter. Then, the solvent is pulled out under a negative pressure to form the dental filling compound.

Example 2

This illustrates the "cold flow" feature of the inventive dental filling materials. A testing method according to an abstract presented at the International Association for Dental Research Convention in Orlando, 2006, Abstract #1442 entitled "Influence of Rheology of Obturating Materials on Lateral Canal Flow" by Karmaker et al, which is hereby incorporated by reference, was used herein. Compositions 1 and 2 from Table 1 were hand molded onto a size 30 obturator carrier after the original gutta percha over-molding coating layer was peeled off to form an inventive "cold flow" filling cone. The new filling cone with the size 30 carrier was then inserted into a clear plastic endodontic trial block (available from Sybron Dental, CA) having a simulated root canal with a lateral thin canal in a perpendicular direction to the main canal at about mid point. The length of the lateral canal penetration by the outer layer coating material was then measured and compared. The deeper the penetration of the coating material, the better the flowability of the material, and thus the greater the potential for better sealing of the filling material. Table 2 below shows the results of the test. The gutta percha and the Resilon® material data were cited from the presentation as references.

TABLE 2

| Material | Initial viscosity in Pascal seconds (Pa s) at 100° C. | Lateral canal flow depth (mm) at heated temperature, unless as indicated |
|---|---|---|
| Gutta Percha on a ThermaFil ™ carrier | 10,045 (202) | 1.1 (0.4) |
| Resilon ® on a ThermaFil carrier | 10,220 (182) | 0 |
| High Flow Resilon ® I on a ThermaFil Carrier | 1,904 (36) | 1.24 (0.10) |
| High Flow Resilon ® II on a ThermaFil Carrier | 9,678 (350) | 1.23 (.07) |
| Inventive Composition 1 on a ThermaFil ™ Carrier | 1,172 (120) | 3.5 (0.5), filled with unheated device at room temperature |
| Inventive Composition 2 on a ThermaFil ™ Carrier | 1,897 (53) | 2.5 (0.5), filled with unheated device at room temperature |

The gutta percha material is based on a polyisoprene polymer, while the Resilon® filing material is based on a polyester polymer. As it can be clearly seen from the illustration above, the inventive dental filling materials based on polybutylene polymers simplify the device application procedure, enhance root canal lateral filling/sealing abilities, eliminate the heating unit, thereby reducing cost and time.

Another example of use for the inventive dental filling compositions herein is for temporary filings and for sealing a tooth cavity. For instance, Composition 1 or 2 in Table 1 above can be packaged in a conventional dental filling material syringe. When in use, a doctor can dispense some material from the syringe and place it into a cavity for temporary sealing to protect any medications underneath for a short duration. Since the inventive material exhibits "cold flow" properties and adapts and adheres to the cavity walls well, the cavity filling material can protect the medication from moisture damage and prevent it from seeping out. Further more, since there is no need for chemical or external energy sources to "cure" the material, the procedure is more efficient and user friendly.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

The invention claimed is:

1. A method for restoring the root canal of a tooth comprising:
    preparing the root canal;
    inserting a filling material into the root canal, wherein the filling material comprises at least 10 weight percent of a polybutylene polymer having a viscosity average molar mass of about 10,000 to about 100,000 g/mol, and being viscoelastic at about 20° C., wherein the filling material fills the root canal and seals the apex of the root canal.
2. The method of claim 1 wherein the filling material is self-leveling at 20° C. when inserting the material into the root canal.

3. The method of claim 1 wherein the filling material is insoluble in water and is dissolvable in a non-polar or polar solvent.

4. The method of claim 1 wherein the filling material further comprises a filler selected from the group consisting of silica, silicate glass, quartz, zinc oxide, barium sulfate, barium silicate, strontium silicate, barium borosilicate, strontium borosilicate, borosilicate, lithium silicate, amorphous silica, bismuth compounds, ammoniated or deammoniated calcium phosphate, alumina, zirconia, tin oxide, titania, and mixtures thereof.

5. The method of claim 1 wherein the filling material further comprises a filler that is a bioactive filler selected from the group consisting of bioglass, calcium phosphate, Portland cement, hydroxyapatite, tricalcium phosphate, a di- or polyphosphonic acid, an anti-estrogen, a substance having a phosphate to calcium ratio similar to natural bone, bone chips, bone crystals, mineral fractions of bone or teeth, and mixtures thereof.

6. The method of claim 1 wherein the filling material further comprises a filler that is an radiopacifying filler selected from the group consisting of apatites, silica glass fillers, calcium silicate based fillers, hydroxyapatites, barium sulfate, bismuth subcarbonate, ytterbium oxide, ytterbium iodine, bismuth oxide, bismuth fluoride, barium oxide tantalum oxide, and mixtures thereof.

7. The method of claim 1 wherein the filling material further comprises glass, ceramic, metal, carbon, graphite, or polymeric fibrous fillers.

8. The method of claim 1 wherein the filling material further comprises a plasticizer selected from the group consisting of polyols, a polyolefins, and mixtures thereof.

9. The method of claim 1 wherein the filling material further comprises an adhesive selected from the group consisting of acrylate adhesives, methacrylate adhesives, and mixture thereof.

10. The method of claim 1 wherein the filling material further comprises a polymeric resin selected from the group consisting of polyamides, polyesters, polyolefins, polyimides, polyarylates, polyurethanes, vinyl esters epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates, triethylene glycol dimethacrylate, polyethylene glycol dimethacrylate, urethane dimethycrylate, hexane diol dimethycrylate, polycarbonate dimethycrylate, the condensation product of bisphenol A and glycidyl methacrylate, 2,2'-bis[4-(3-methacryloxy-2-hydroxy propoxy)-phenyl]-propane and mixtures thereof.

11. A method for restoring the root canal of a tooth comprising:
preparing the root canal;
inserting a filling material into the root canal, wherein the filling material comprises at least 40 percent by weight polybutylene polymer having a viscosity average molar mass of about 10,000 to about 100,000 and being viscoelastic at about 20° C.

12. A method for restoring the root canal of a tooth comprising:
preparing the root canal;
inserting a filling material into the root canal, wherein the filling material comprises at least 10 weight percent polybutylene polymer having a viscosity average molar mass of about 10,000 to about 100,000 g/mol, and being viscoelastic at about 20° C. and wherein the filling material is in the form of a cone to be inserted into the root canal or fabricated into a dental obturator or endodontic post.

13. The method of claim 12 wherein, in an obturator or endodontic post, an outer layer is fabricated of the filler material a core section is made of a different material to give support to the outer layer.

14. The method of claim 13 wherein, in an obturator, the core section forms a shaft of an obturator and the outer layer forms the filling material or, in an endodontic post, the core section forms the post section of the past and the outer layer section forms a filling tip section of the post.

15. The method of claim 12 wherein preparation of the root canal comprises applying to the walls of the root canal an etchant, bonding agent, or sealant.

16. The method of claim 12 wherein the sealing filing material flows into the crevices and accessory canals in the root canal and forms intimate contact with the surface adjacent to it.

17. The method of claim 12 wherein the root canal filling material, after filling the root canal, has dissolvabilty and retrievability.

18. The method of claim 12 wherein the filling material is inserted without heating to soften it, thereby eliminating volume shrinkage due to melting and cooling.

19. The method of claim 12 wherein the filling material further comprises a bismuth compound that provides radiopacity.

* * * * *